(12) United States Patent
Monsonego et al.

(10) Patent No.: US 9,664,690 B1
(45) Date of Patent: May 30, 2017

(54) MOLECULAR DIAGNOSTIC KITS FOR EVALUATING STRESS

(71) Applicant: The National Institute for Biotechnology in the Negev Ltd., Beersheba (IL)

(72) Inventors: Alon Monsonego, Beersheba (IL); Idan Harpaz, Beersheba (IL)

(73) Assignee: THE NATIONAL INSTITUTE FOR BIOTECHNOLOGY I, Beersheba (IL)

( * ) Notice: Subject to any disclaimer, the term of this patent is extended or adjusted under 35 U.S.C. 154(b) by 0 days.

(21) Appl. No.: 14/471,168

(22) Filed: Aug. 28, 2014

Related U.S. Application Data

(60) Provisional application No. 61/870,795, filed on Aug. 28, 2013.

(51) Int. Cl.
*G01N 33/68* (2006.01)
*G01N 33/50* (2006.01)
*G01N 33/74* (2006.01)

(52) U.S. Cl.
CPC ..... *G01N 33/6863* (2013.01); *G01N 33/5091* (2013.01); *G01N 33/5094* (2013.01); *G01N 33/6866* (2013.01); *G01N 33/6869* (2013.01); *G01N 33/6872* (2013.01); *G01N 33/743* (2013.01); *G01N 2333/723* (2013.01); *G01N 2800/24* (2013.01); *G01N 2800/2821* (2013.01); *G01N 2800/302* (2013.01); *G01N 2800/304* (2013.01); *G01N 2800/7004* (2013.01)

(58) Field of Classification Search
CPC ........... G01N 33/5094; G01N 33/6863; G01N 33/6872; G01N 33/5091; G01N 33/6866; G01N 33/6869; G01N 33/743; G01N 2800/24; G01N 2800/2821; G01N 2800/304; G01N 2800/302; G01N 2800/7004; G01N 2333/723
See application file for complete search history.

(56) References Cited

U.S. PATENT DOCUMENTS

| | | | | |
|---|---|---|---|---|
| 2005/0265993 | A1* | 12/2005 | Mach | C07K 16/2809 424/141.1 |
| 2008/0155704 | A1* | 6/2008 | Panayi | G01N 33/68 800/3 |

* cited by examiner

*Primary Examiner* — Gail R Gabel
(74) *Attorney, Agent, or Firm* — The Roy Gross Law Firm, LLC; Roy Gross

(57) ABSTRACT

A diagnostic kit for evaluating stress hormones, and methods of use and manufacture thereof.

24 Claims, 7 Drawing Sheets

MOLECULAR DIAGNOSTIC KITS FOR EVALUATING STRESS

FIELD OF THE INVENTION

The present invention relates to molecular diagnostic kits for evaluating stress, and methods of use and manufacture thereof.

BACKGROUND OF THE INVENTION

It has been well established that stress may substantially affect the homeostatic regulation of the immune system. In most animal models studied thus far, stressful triggers such as fear, maternal deprivation, social threat, or physiological challenge have been shown to induce immunosuppression associated with increased susceptibility to allergies and infectious diseases. These effects are mediated by the hypothalamic-pituitary-adrenal (HPA) axis, a complex network linking the nervous, endocrine and immune systems. The HPA axis can be triggered by stress or by proinflammatory cytokines (e.g. IL-1, IL-6, and TNF-α) to ultimately result in the secretion of corticosterone (CORT) from the adrenal glands to the circulation.

CORT, in turn, acts to suppress the activation, proliferation, and trafficking of immune cells and plays a role in autoimmune regulation via shifting from Th1/Th17 pro-inflammatory to Th2 antiinflammatory responses. Indeed, previous studies have shown that rats producing lower CORT levels (e.g. due to genetic manipulation or adrenalectomy) are more susceptible to pathogenic autoimmunity. CORT is therefore often used as an immunosuppressor in the clinical treatment of inflammatory and autoimmune diseases.

Regardless of the immunosuppressive effects of CORT, chronic exposure to stress has also been linked with relapse of autoimmune diseases such as multiple sclerosis and psoriasis. Paradoxically, these diseases are characterized by a Th1/Th17 pro-inflammatory immune response, which implies that chronic stress exposure attenuates the immunosuppressive effects of CORT. It has also been suggested that CORT may affect regulatory T (Treg) cells which play a central role in protecting against autoimmune diseases.

SUMMARY

The background art does not teach or suggest a diagnostic kit for evaluating stress, and methods of use and manufacture thereof.

The present invention, in at least some embodiments, overcomes these drawbacks of the background by art by providing a diagnostic kit for evaluating stress, and methods of use and manufacture thereof.

The present inventors have shown that chronic exposure to stress predisposes higher autoimmune susceptibility in C57BL/6 mice, such that glucocorticoids may be described as a double-edged sword (Harpaz et al, Eur. J. Immunol. 2013. 43: 758-769). In this study, the inventors demonstrated that chronic variable stress (CVS), and the associated alterations in CORT levels, affect the susceptibility to experimental autoimmune encephalomyelitis (EAE) in female and male C57BL/6 mice. Under baseline (nonstressed) conditions, females exhibited substantially higher CORT levels and an attenuated EAE with less mortality than males. However, CVS induced a significantly worsened EAE in females, which was prevented if CORT signaling was blocked. In addition, females under CVS conditions showed a shift toward proinflammatory Th1/Th17 versus Th2 responses and a decreased proportion of CD4+CD25+ Treg cells. This demonstrates that whereas C57BL/6 female mice generally exhibit higher CORT levels and an attenuated form of EAE than males, they become less responsive to the immunosuppressive effects of CORT under chronic stress and thereby prone to a higher risk of destructive autoimmunity.

According to at least some embodiments, the kit evaluates immune system functioning and impacts on medical conditions associated with stress, depression, cancer, senescence, neurodegeneration and autoimmune diseases.

The kit is based on data from the present inventors which measures an attenuated response of individuals to the immunosuppressive effects of glucocorticoids (GCs), described briefly above and in greater detail below.

GCs play a crucial role in regulating the immune responses and thus, consequently suppress pathogenic stimulation of the immune system. GCs regulate immune responses primarily via glucocorticoid receptors (GRs) which are highly expressed among activated leukocytes. Following ligand binding, GC-GR complex translocates into the nucleus and generally suppress inflammation by selectively inducing immune-cell apoptosis. This in turn, eventually increases the frequency of regulatory T cells which act to suppress the activities of effector T cells and within the effector subsets, shifts from TH1/TH17 pro- to TH2 antiinflammatory immune responses and thus maintain homeostasis. Indeed GCs deficiency and glucocorticoid receptor dysfunction have been associated with excessive inflammatory and autoimmune diseases. Therefore, early diagnoses and treatment of GCs resistance among immune cells in the periphery can be essential to treat and prevent the development of stress and inflammatory related diseases and thus may prevent many chronic illnesses and increase the longevity and quality of life.

According to at least some embodiments, there is provided a kit for diagnosis or detection of stress and/or hormone resistance, such as GC resistance for example, and/or immune system function or level, comprising detecting one or more of the following biomarkers.

One example of such a biomarker is increased steroid resistance of an immune cell subset. By "increased steroid resistance" it is meant in comparison to a subject not suffering from the condition described, such as stress, or having a normal condition, for example for immune responsiveness. Indeed the terms "increased" or "decreased" with regard to the assay results are determined according to such a comparison with a normal subject or a subject not suffering from the condition under test.

Such increased resistance may optionally be determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody.

For example, this may be performed by detecting steroid resistance of immune cell subsets via measuring the immunosuppressive effect of MP on pro-inflammatory cytokine secretion following in vitro stimulation (anti-CD3 for T cells and LPS for monocytes and dendritic cells).

Another example of such a biomarker is a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining.

Another example of such a biomarker is increased GRbeta/GRalpha ratio in chronically stressed individuals, which is the ratio of these two forms of the glucocorticoid receptor (GR). As described in greater detail below, it is expected that when individuals experience chronic stress, the level of GRbeta increases and/or the level of GRalpha decreases, such that the overall ratio increases.

Yet another example of such a biomarker is an increased GRbeta/GRalpha ratio, determined by detecting a level of each isoform in a sample taken from the subject with an antibody covalently bound to a detectable marker, such that said level of each isoform corresponds to a level of covalently bound antibody.

Still another example of such a biomarker is a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody.

A further example of such a biomarker relates to measurements of bound and free glucocorticoids in the serum, urine or saliva. Such measurements are well known in the art; for example, such measurements may optionally be performed through a standard medical laboratory test. According to at least one embodiment of the present invention, one or both of bound and free glucocorticoids are increased or decreased.

The kit preferably involves measuring a plurality of the above biomarkers in the subject to form a plurality of biomarker measurements. Any combination of such biomarkers may optionally be measured as part of the kit. Also optionally, all biomarkers may be measured as part of the kit.

Each of these measurements is preferably performed with an assay, such that the reagents and processes described herein are preferably provided through an assay for each measurement.

The kit is optionally and preferably suitable for use with a detector for measuring the plurality of biomarkers in the subject to form a plurality of biomarker measurements according to the assay.

The kit is also optionally and preferably suitable for use with an analyzer for analyzing said plurality of biomarker measurements to determine an impact on the immune system, wherein detecting an existence of said plurality of biomarker measurements indicates a decreased level of immune system responsiveness.

It should be noted that while the above specific measurements may optionally be used for determining immune system responsiveness and/or a level of chronic stress, corresponding biomarkers described below may optionally be substituted or added to determine a level of aging of the immune system, and may optionally even be used to consider a prognosis or diagnosis of Alzheimer's disease as described below.

According to at least some embodiments, there is provided a kit for evaluating immune system functioning in a subject, comprising a set of assays for measuring a plurality of biomarkers in the subject to form a plurality of biomarker measurements, said assays selected from the group consisting of:

an assay for determining increased steroid resistance of an immune cell subset, determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody;

an assay for determining a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining;

an assay for determining an increased GRbeta/GRalpha ratio, determined by detecting a level of each isoform in a sample taken from the subject with an antibody covalently bound to a detectable marker, such that said level of each isoform corresponds to a level of covalently bound antibody;

an assay for determining a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody; or an assay for determining measurements of bound and free glucocorticoids in one or more of serum, urine or saliva in a sample taken from the subject; wherein detecting an existence of said plurality of biomarker measurements indicates a decreased level of immune system responsiveness to a glucocorticoid or a glucocorticoid receptor agonist.

Optionally said assay for said measuring said level of said steroid resistance of immune cell subsets further comprises measuring an immunosuppressive effect of MP (methylprednisolone) on said level of said pro-inflammatory cytokine secretion following said in vitro stimulation of said at least one immune cell subset taken from the subject, wherein chronic stress is associated with a decreased immunosuppressive effect of MP on said level of pro-inflammatory cytokine secretion as determined according to said level of covalently bound antibody.

Optionally and preferably, said at least one immune cell subset comprises T cells and said in vitro stimulation comprises contacting said T cells with anti-CD3 and anti-CD28 in solution or on beads with both antibodies.

Also optionally and preferably, said at least one immune cell subset comprises monocytes and said in vitro stimulation comprises contacting said monocytes with LPS (lipopolysaccharide) or other toll-like receptor (TLR) ligands or compounds which can stimulate monocytes and/or dendritic cells.

Also optionally and preferably, said at least one immune cell subset comprises dendritic cells and said in vitro stimulation comprises contacting said dendritic cells with LPS (lipopolysaccharide).

Optionally said decreased Tregs/Teff ratio is determined according to a decreased level of Tregs in the subject as determined according to said assay.

Optionally a greater number of positively detected biomarker measurements indicates a more decreased level of immune system responsiveness.

Optionally the kit further comprises a detector for measuring the plurality of biomarkers in the sample from the subject according to each assay to form a plurality of biomarker measurements.

Optionally the kit further comprises an analyzer for analyzing said plurality of biomarker measurements to determine an impact on the immune system, wherein detecting an existence of said plurality of biomarker measurements indicates a decreased level of immune system responsiveness to said glucocorticoid or said glucocorticoid receptor agonist.

Optionally and preferably, said glucocorticoid or said glucocorticoid receptor agonist is at least one of cortisol, dexamethasone or methylprednisolone.

Optionally and more preferably, a greater number of positively detected biomarker measurements by said analyzer indicates a more decreased level of immune system responsiveness.

Optionally said measurements from said assays of said biomarkers further correlate with chronic stress in the subject.

Optionally said immune responsiveness further correlates with at least one of a mental condition, an autoimmune disease, chronic inflammation or glucocorticoid resistance associated with a tumor or tumor micro-environment.

Optionally and preferably, said mental condition is selected from the group consisting of Alzheimer's, depression, schizophrenia and aging.

According to at least some embodiments, there is provided a kit for assessing a mental condition in a subject, comprising a set of assays for measuring a plurality of biomarkers in the subject to form a plurality of biomarker measurements, said assays selected from the group consisting of:

an assay for determining increased steroid resistance of an immune cell subset, determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody;

an assay for determining a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining;

an assay for determining an increased GRbeta/GRalpha ratio, determined by detecting a level of each isoform in a sample taken from the subject with an antibody covalently bound to a detectable marker, such that said level of each isoform corresponds to a level of covalently bound antibody;

an assay for determining a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody; or an assay for determining measurements of bound and free glucocorticoids in one or more of serum, urine or saliva in a sample taken from the subject; wherein detecting an existence of said plurality of biomarker measurements provides an assessment of said mental condition in the subject.

Optionally said mental condition is selected from the group consisting of Alzheimer's, depression, schizophrenia and aging.

According to at least some embodiments, there is provided a kit for evaluating a level of stress in a subject, comprising a set of assays for measuring a plurality of biomarkers in the subject to form a plurality of biomarker measurements, said assays selected from the group consisting of:

an assay for determining a decreased level of steroid resistance of an immune cell subset, determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody;

an assay for determining a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining;

an assay for determining an increased GRbeta/GRalpha ratio, determined by detecting a level of each isoform in a sample taken from the subject with an antibody covalently bound to a detectable marker, such that said level of each isoform corresponds to a level of covalently bound antibody;

an assay for determining a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody; or an assay for determining measurements of bound and free glucocorticoids in one or more of serum, urine or saliva in a sample taken from the subject; wherein detecting an existence of said plurality of biomarker measurements indicates said level of stress in the subject.

Optionally a greater extent of said biomarker measurements indicates an increased level of said stress in the subject.

Optionally a greater number of positively detected biomarker measurements indicates an increased level of said stress in the subject.

Optionally said stress is chronic stress.

According to at least some embodiments, there is provided a method for evaluating immune system functioning in a subject, comprising performing a set of assays for measuring a plurality of biomarkers in the subject to form a plurality of biomarker measurements, said assays selected from the group consisting of:

an assay for determining increased steroid resistance of an immune cell subset, determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody;

an assay for determining a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining;

an assay for determining an increased GRbeta/GRalpha ratio, determined by detecting a level of each isoform in a sample taken from the subject with an antibody covalently bound to a detectable marker, such that said level of each isoform corresponds to a level of covalently bound antibody;

an assay for determining a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody; or an assay for determining measurements of bound and free glucocorticoids in one or more of serum, urine or saliva in a sample taken from the subject; wherein detecting an existence of said plurality of biomarker measurements indicates a decreased level of immune system responsiveness to a glucocorticoid or a glucocorticoid receptor agonist.

According to at least some embodiments, there is provided a method for assessing a mental condition in a subject, comprising performing a set of assays for measuring a plurality of biomarkers in the subject to form a plurality of biomarker measurements, said assays selected from the group consisting of:

an assay for determining a decreased level of steroid resistance of an immune cell subset, determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody;

an assay for determining a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining;

an assay for determining an increased GRbeta/GRalpha ratio, determined by detecting a level of each isoform in a sample taken from the subject with an antibody covalently bound to a detectable marker, such that said level of each isoform corresponds to a level of covalently bound antibody;

an assay for determining a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody; or an assay for determining measurements of bound and free glucocorticoids in one or more of serum, urine or saliva in a sample taken from the subject; wherein detecting an existence of said plurality of biomarker provides an assessment of said mental condition in the subject.

According to at least some embodiments, there is provided a method for evaluating a level of stress in a subject, comprising performing a set of assays for measuring a plurality of biomarkers in the subject to form a plurality of biomarker measurements, said assays selected from the group consisting of:

an assay for determining increased steroid resistance of an immune cell subset, determined by detecting a level of pro-inflammatory cytokine secretion following in vitro stimulation of at least one immune cell subset in a sample taken from the subject and application of a steroid to said at least one immune cell subset, wherein said detecting said pro-inflammatory cytokine secretion comprises contacting said secretion with an antibody covalently bound to a detectable marker; and determining said level of pro-inflammatory cytokine in said secretion according to a level of covalently bound antibody;

an assay for determining a decreased Tregs/Teff ratio, determined by harvesting peripheral blood lymphocytes (PBLs) from a blood sample from the subject, staining said PBLs for CD4, CD25 and CD127, and determining a level of Tregs and a level of Teff according to said staining;

an assay for determining an increased GRbeta/GRalpha ratio, determined by detecting a level of each isoform in a sample taken from the subject with an antibody covalently bound to a detectable marker, such that said level of each isoform corresponds to a level of covalently bound antibody;

an assay for determining a decreased level of immune cell responsiveness in an immune cell subset to a GR antagonist, determined by detecting a level of pro-inflammatory cytokine secretion following in vitro stimulation of at least one immune cell subset in a sample taken from the subject and application of a GR antagonist and a steroid, wherein said detecting said pro-inflammatory cytokine secretion comprises contacting said secretion with an antibody covalently bound to a detectable marker; and determining said level of pro-inflammatory cytokine in said secretion according to a level of covalently bound antibody; or an assay for determining measurements of bound and free glucocorticoids in one or more of serum, urine or saliva in a sample taken from the subject; wherein detecting an existence of said plurality of biomarker measurements indicates said level of stress in the subject.

Unless otherwise defined, all technical and scientific terms used herein have the same meaning as commonly understood by one of ordinary skill in the art to which this invention belongs. The materials, methods, and examples provided herein are illustrative only and not intended to be limiting.

DESCRIPTION OF SOME EXEMPLARY EMBODIMENTS

The present invention, in at least some embodiments, provides a diagnostic kit for evaluating stress, and methods of use and manufacture thereof.

Example 1—Effect of Chronic Endogenic Steroid Exposure in Mice

As described in greater detail below, the experimental data shows that individuals that undergo chronic exposure to endogenic steroids (namely, chronic stressed mice, aged human and mice and autoimmune patients) demonstrate resistance to the immunosuppressive effects of MP (methylprednisolone) associated with increased inflammatory environment.

Peripheral blood lymphocytes were stimulated in 96-well culture plate ($2\times10^5$ cells/well) with plate bound anti-CD3 mAb (0.5 µg/ml), and cultured for 48 h at 37° C. The cultured supernatants were removed and stored at 80° C. Cytokine concentration in the supernatants were measured by ELISA using human cytokine kits.

Results

Figure 1:
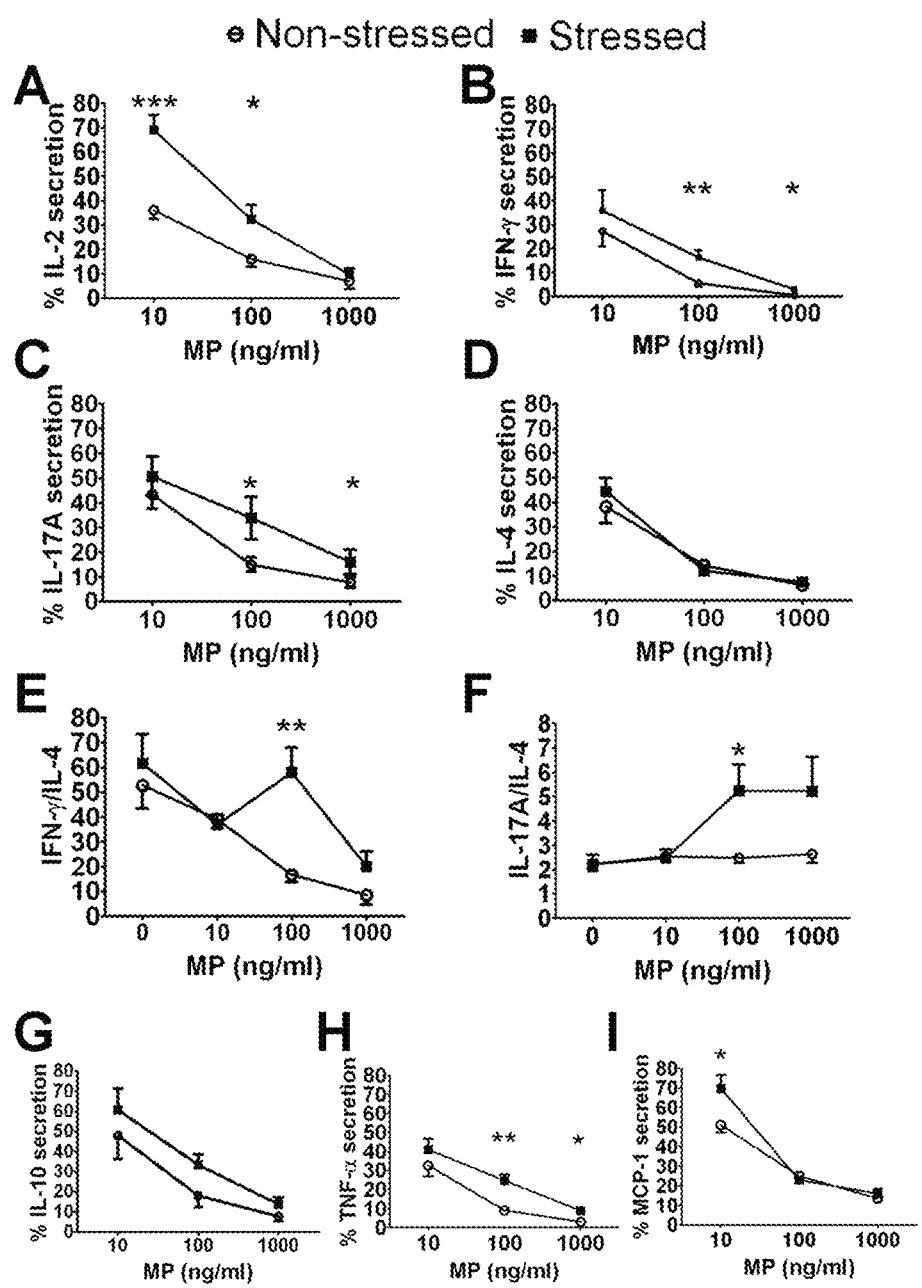
FIGS. 1A-I. Chronic stress promotes decreased T-cell sensitivity to MP. Line graphs showing levels in the supernatant of cytokines (1A) IL-2, (1B) IFNγ, (1C) IL-17A, (1D) IL-4, (1E) IFNγ standardized to IL-4, and (1F) IL-17A standardized to IL-4, (1G) IL-10, (1H) TNFα, and (1I) MCP-1 from stressed and non-stressed cells after treatment with MP. Cytokines in the supernatant were measured by ELISA.

CVS (chronic variable stress), as a model for chronic stress in humans, promotes Th1/Th17 effector functions associated with decreased T-cell sensitivity to the immunosuppressive effects of MP, as shown in FIG. 1.

Splenocytes were harvested from stressed and non-stressed female mice, stimulated in vitro with plate-bound anti-CD3 for 48 hours with or without methylprednisolone (MP) (10, 100 or 1000 ng/ml). Cytokine production was measured in supernatant by ELISA (A-D, G-I) and is shown as percentage of the levels measured without MP. IFN-γ/IL-4 and IL-17/IL-4 ratios were calculated (E-F).

Figure 2:
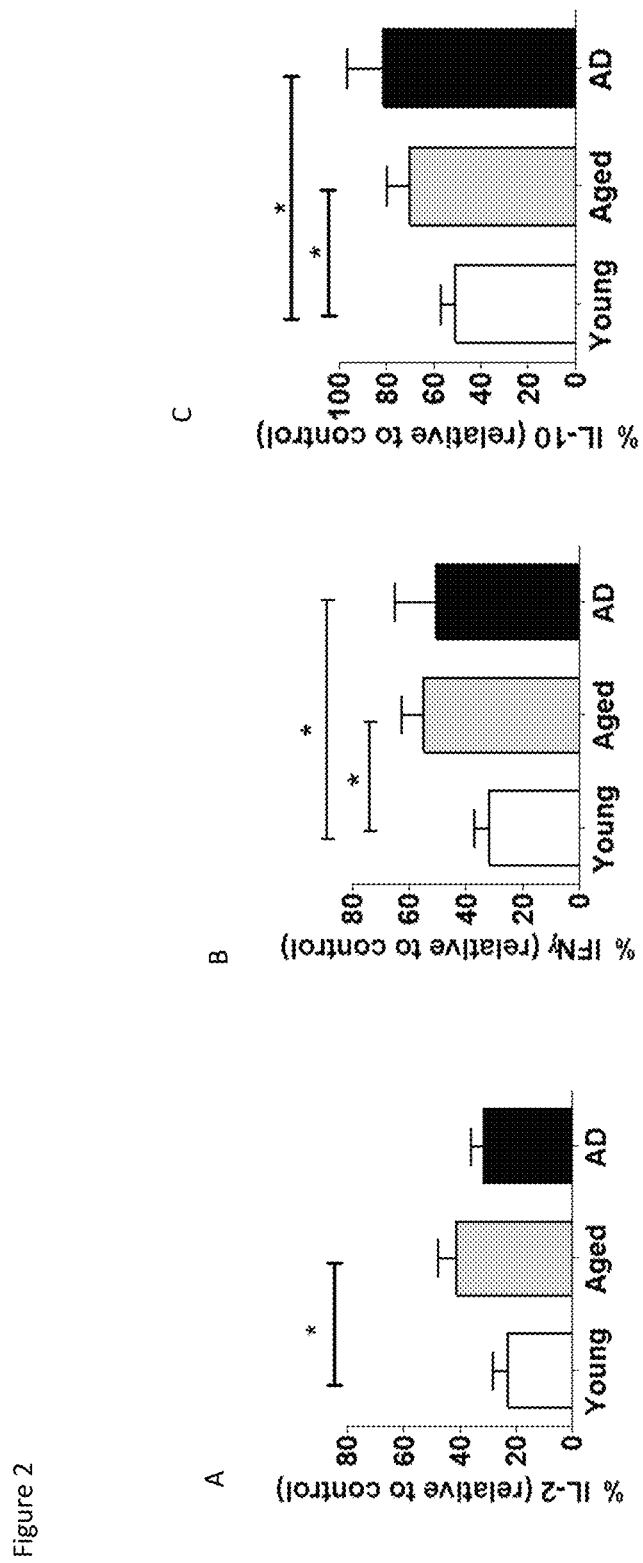
FIGS. 2A-C. Aging and Alzheimer's disease mimic chronic stress. Bar charts depicting (2A) IL-2, (2B) IFNγ, and (2C) IL-10 levels in the supernatant from young and aged healthy cells and from Alzheimer's disease (AD) cells. Results are standardized to levels in control cells.

Aging (including Alzheimer disease patients, (AD)) which mimics some features of stress in term of high endogenic steroid level also induces steroid resistance among immune cells as shown in FIG. 2. Aging generally decreases the sensitivity of stimulated PBMCs to the immunosuppressive effects of MP. PBMCs were purified from young, aged and AD patients and stimulated with plate-bound anti-CD3 for 48 hours in the present of the synthetic steroid, methylprednisolone (MP). Cytokine production was measured in supernatant by ELISA and is shown as percentage of the levels measured without MP (A-D). (A) IL-2 (B) IFN-g (C) IL-10.

Figure 3:
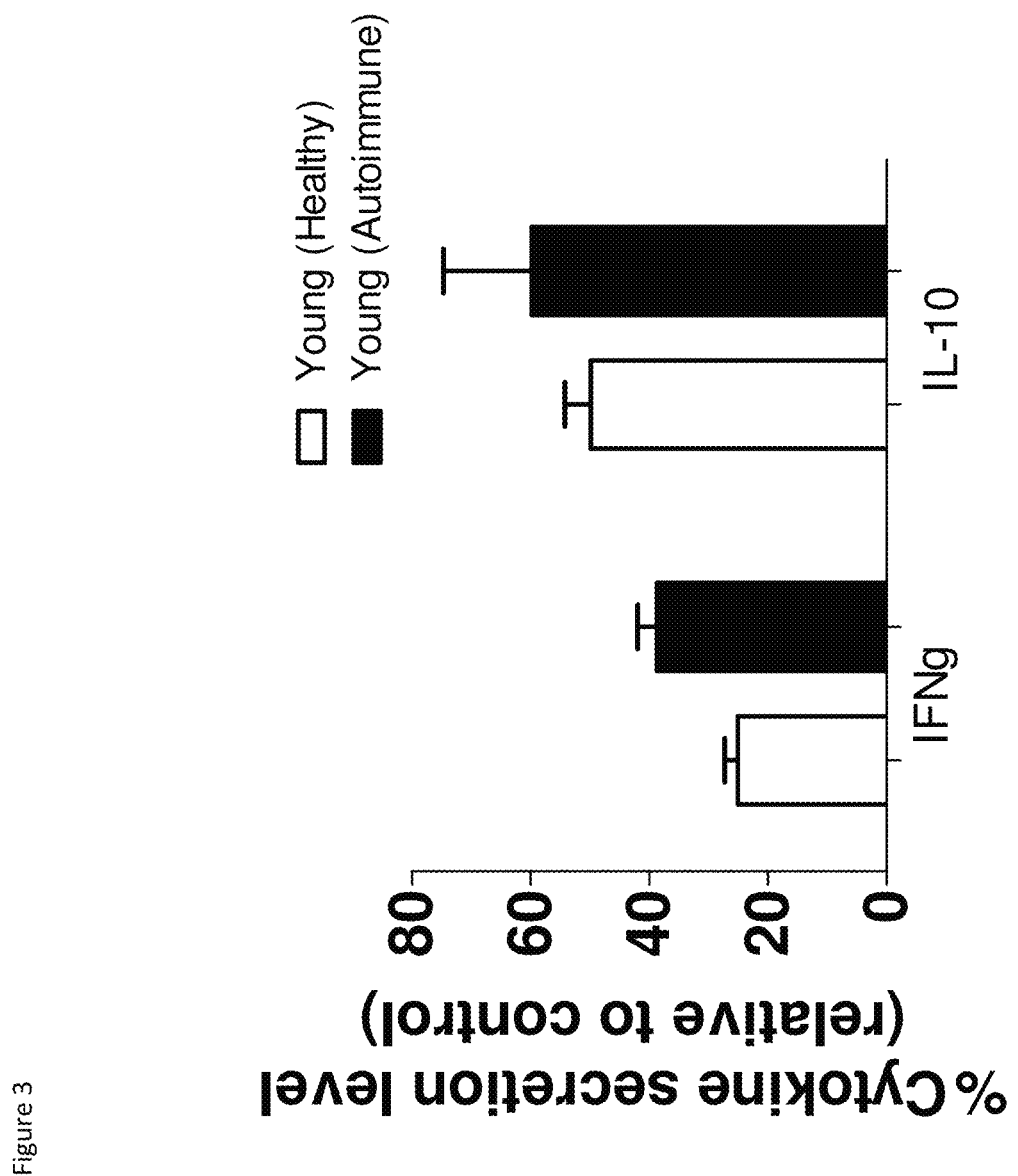
FIG. 3. Autoimmune disease mimics chronic stress. Bar chart of cytokine levels in the supernatant of health and autoimmune cells.

The autoimmune disease state is also characterized by the secretion of high level of endogenous steroids. The below data in FIG. 3 shows that patients with autoimmune diseases demonstrated impaired immunosuppressive effect of MP (cortisol analogue) on immune cell subsets following stimulation, mainly among inflammatory producing cells such as IFNg. Specifically, FIG. 3 shows steroid resistance among healthy young subjects as compared to subjects with autoimmune disorder.

Figure 4:
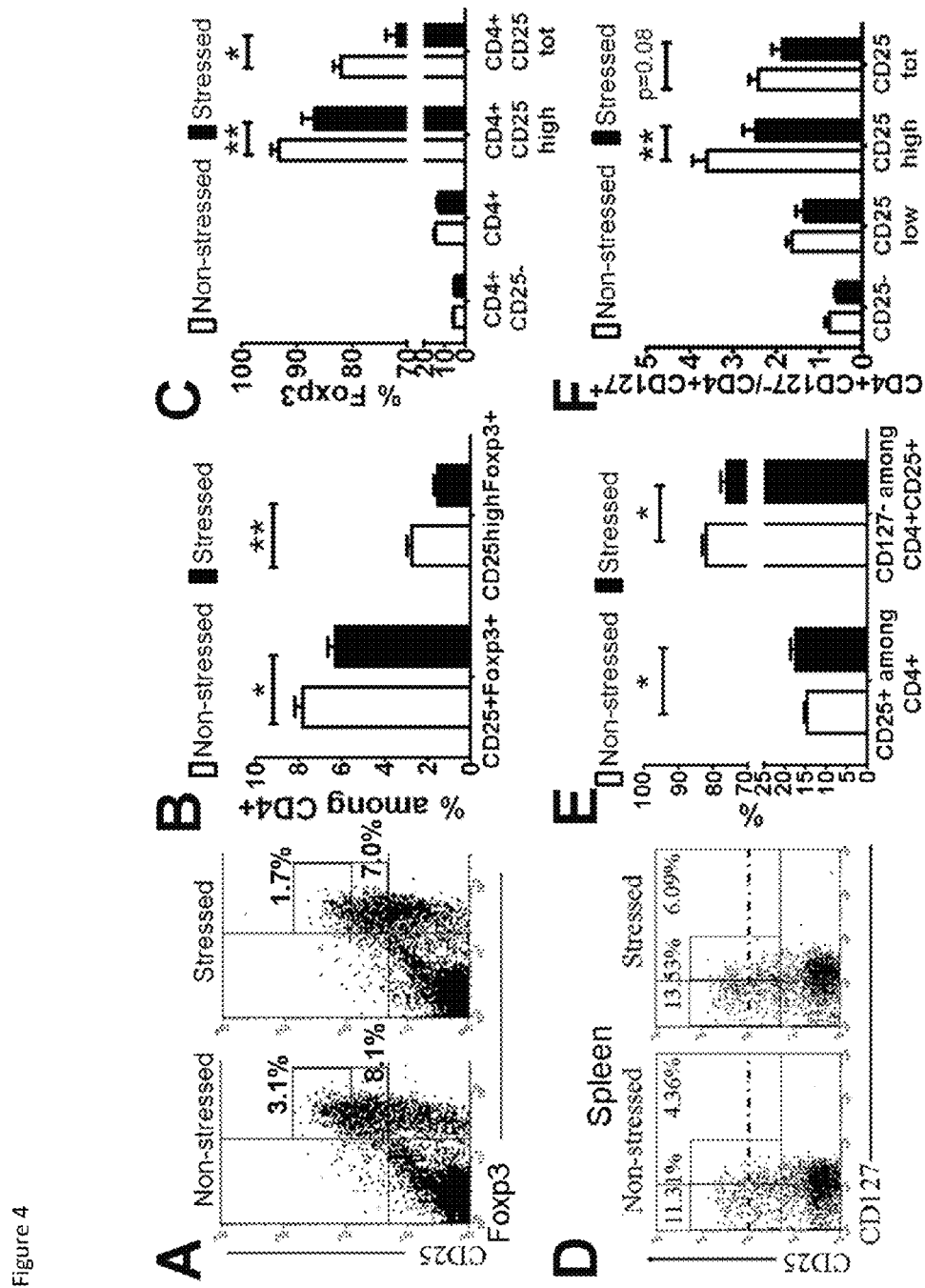
FIGS. 4A-F. Chronic stress promotes decreased Treg to Teff ratio in the spleen. (4A) Dot plot depicting a reduced frequency of splenic regulatory T-cells in stressed mice. (4B) Bar chart depicting the reduction of CD25 positive and CD25 highly expressing cells in the spleen of stressed mice. (4C) Bar chart depicting the reduction of Foxp3 positive cells in the spleen of stressed mice. (4D) Dot plot depicting the populations of regulatory and effector T-cells in the spleen of stressed and non-stressed mice. (4E) Bar chart depicting the populations of regulatory and effector T-cells in the spleen of stressed and non-stressed mice. (4F) Bar chart depicting the populations of regulatory and effector T-cells relative to CD25 expression in the spleen of stressed and non-stressed mice.

The effect of stress was demonstrated to alter the proportion between immune cell subsets that control inflammation (Regulatory t cells; Tregs) and those who accelerate it (Effector T cells; Teff) Immune cells were harvested from stressed and non-stressed female mice, stained for CD4, CD25 and Foxp3 or CD4, CD25 and CD127 and subsequently analyzed by flow cytometry. FIG. 4 shows that living in chronic stress environment contributes to decreased Tregs/Teff ratio in the spleen.

FIG. 4 shows that chronic stress reduces the frequency of splenic regulatory T-cells. Splenocytes were harvested from stressed and non-stressed female mice, stained for CD4, CD25 and Foxp3 (A-C, H) or CD4, CD25 and CD127 (D-G), and subsequently analyzed by flow cytometry. (A-B) Splenocytes were gated for CD4+ T cells and then analyzed for the frequency of CD25+Foxp3+ and CD25highFoxp3+ T cells. (C) The frequency of Foxp3+ cells among CD4+ T cells. (D-E) Analysis of CD4+CD25+ T cells and the frequency of CD127− cells among CD4+CD25+ T cells. (D,F) The CD127−/CD127+ ratio within CD4+ T cells. (G) The frequency of CD25+CD127+ and CD25+CD127− cells among CD4+ T cells.

Figure 5:
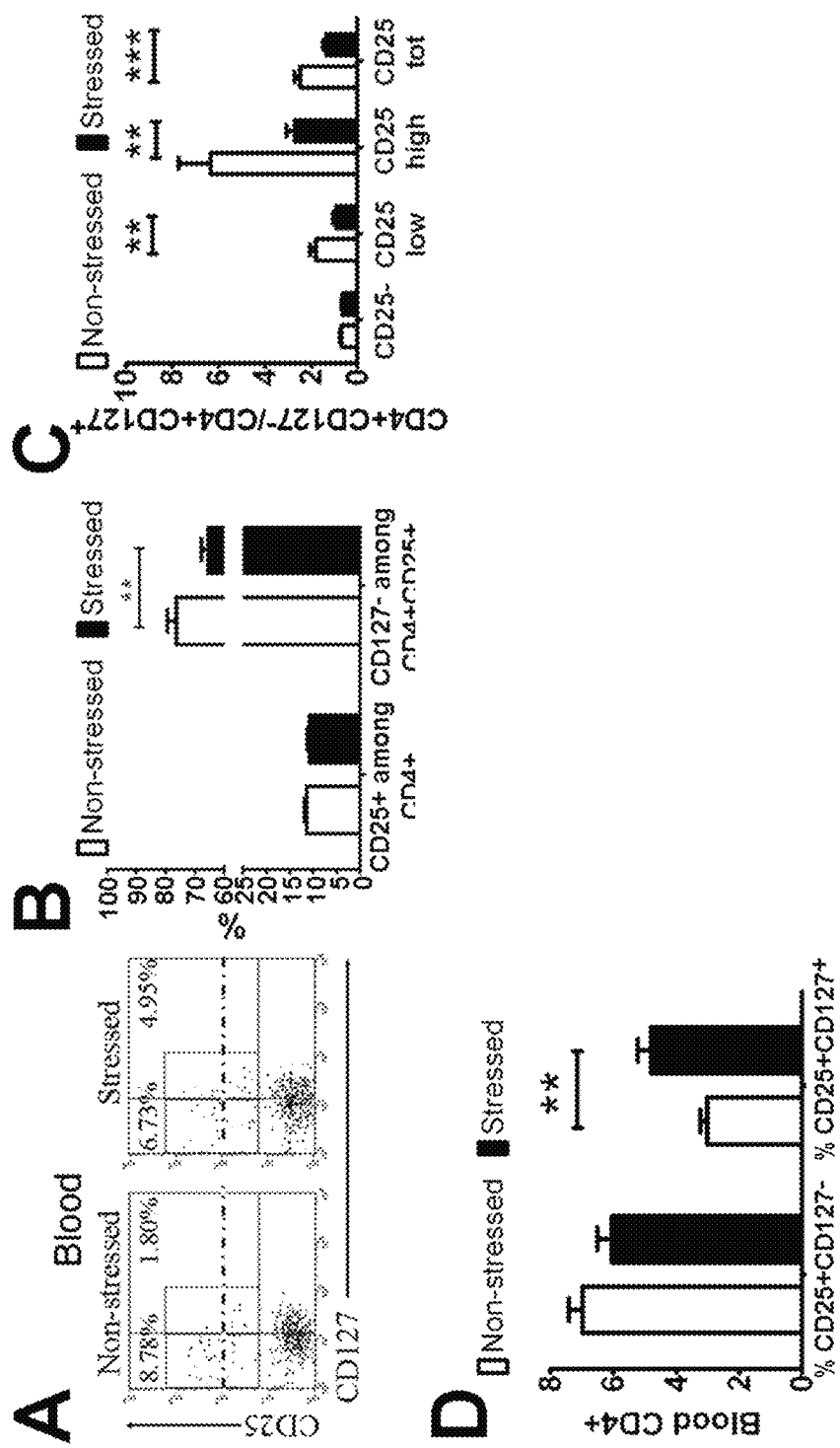
FIGS. 5A-D. Chronic stress promotes decreased Treg to Teff ratio in the blood. (5A) Dot plot depicting the populations of regulatory and effector T-cells in the blood of stressed and non-stressed mice. (5B) Bar chart depicting the populations of regulatory and effector T-cells in the blood of stressed and non-stressed mice. (5C) Bar chart depicting the populations of regulatory and effector T-cells relative to CD25 expression in the blood of stressed and non-stressed mice. (5D) Bar chart depicting the percentage of CD4 positive cells that are regulatory and effector T-cells in the blood of stressed and non-stressed mice.

FIG. 5 shows that exposure to chronic variable stress (CVS) decreases Tregs/Teff ratio in the blood. FIG. 5 shows that CVS reduces the frequency of blood-derived regulatory T-cells. Blood samples were drawn from both non-stressed and stressed mice before and following EAE. Peripheral blood lymphocytes (PBLs) were then harvested, stained for CD4, CD25 and CD127 and subsequently analyzed by flow cytometry. (A-B) Analysis of CD4+CD25+ T cells. (A-B) The frequency of CD127− cells among CD4+CD25+ T cells. (C) The CD127−/CD127+ ratio within the CD4+ T-cell subsets. (D) The frequency of CD25+CD127+ and CD25+CD127− cells among CD4+ T cells.

Figure 6:
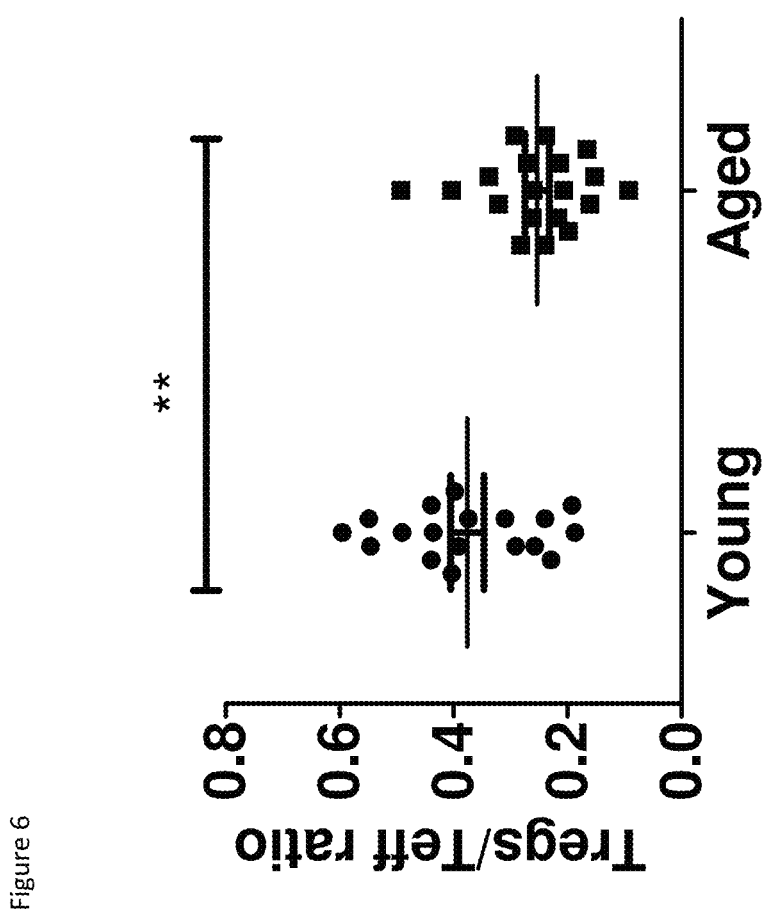
FIG. 6. Aging promotes decreased Treg to Teff ratio in the blood. Scatter plot of the ratio of regulator T-cells to effector T-cells in the blood of young and aged mice.

FIG. 6 shows increased Teff/Tregs ratio among aged subjects. FIG. 6 shows the effect of aging and on CD4+ Teff/Tregs ratio. PBMCs were purified from young and healthy-aged subjects, stained for CD4, CD25 and CD127, and subsequently analyzed by flow cytometry to evaluate the Tregs/Teff ratio.

Example 2—In Vitro Evaluation of Effects of Stress on Immune Cell Function

Immune cells from human (PBMCs) or mice (splenocytes) are purified and analyzed as follows, to determine biomarkers for the stress diagnostic kit of the present invention in at least some embodiments thereof.

To evaluate the effects of stress on immune cell function and regulation, PBMCs are suspended with RPMI medium and stimulated by plate-bound anti-CD3 mAb (0.5 micro-g/ml) for 48 hours or by LPS (lipopolysaccharide, 100 ng/ml) for 24 hours at 37° C. in the presence or absence of methylpredenisolone (MP) (10, 100, 1000 and 10000 ng/ml) which is clinically used for the treatments of chronic inflammatory and autoimmune diseases. The cultured supernatants are removed and stored at 80° C. Both adaptive and innate cytokine concentration in the supernatants are measured by ELISA using cytokine kits (IL-1a, IL-1b, IL-6, TNFa, IL-2, IL-4, IL-10, IL-17, IL-12, IL-22, MCP1, RANTS, etc).

Example 3—GR Isoforms

The human GR (glucocorticoid receptor) population contains two isoforms, GR-alpha and GR-beta. GR-alpha is the classically functional GR, while GR-beta seems to act as a dominant negative to the function of GR-alpha. Previous studies have shown that the ratio between these two isoforms may determine the responsiveness of immune cells to the immunosuppressive effect of glucocorticoids. Thus, an experiment will be performed to determine whether exposure to chronic stress can shift the ratio into the GR-beta isoform, which could therefore act as an additional biomarker(s) for the inventive stress evaluation kit, according to at least some embodiments thereof.

In order to investigate the effect of stress on GR-alpha/GR-beta ratio, immune cells from non-stressed and stressed individuals will be examined by Western blot for the presence of these two GR isoforms. These two GR isoforms can also be optionally separately detected through an ELISA directly with an antibody covalently bound to a detectable marker. In either case, each form is bound, directly or indirectly, with an antibody covalently bound to a detectable marker, in order for the level of each form to be measured.

It is expected that the level of GRalpha will decrease and/or the level of GRbeta will increase, such that the ratio of GRbeta/GRalpha will increase overall. These results demonstrate the importance of this ratio and its utility as part of a kit according to at least some embodiments of the present invention.

Example 4—Immune Cell Responsiveness

Another approach to investigate the functionality of GR is by the examination of the responsiveness of immune cell subsets to the glucocorticoid antagonist, mifepristone. According to experiments performed as described in Example 1, the data in FIG. 7 demonstrate that whereas mifepristone partially blocks the MP immunosuppressive effects following in-vitro stimulation of PBMCs in young subjects, it is impaired in both aged and Alzheimer's disease (AD) subjects. This indicates an impairment in GR signaling which contributes to steroid resistance, which could be tested in stressed and non-stressed individuals as described herein. Such an impairment could also optionally act as a biomarker for the stress diagnostic kit according to at least some embodiments thereof.

Figure 7:
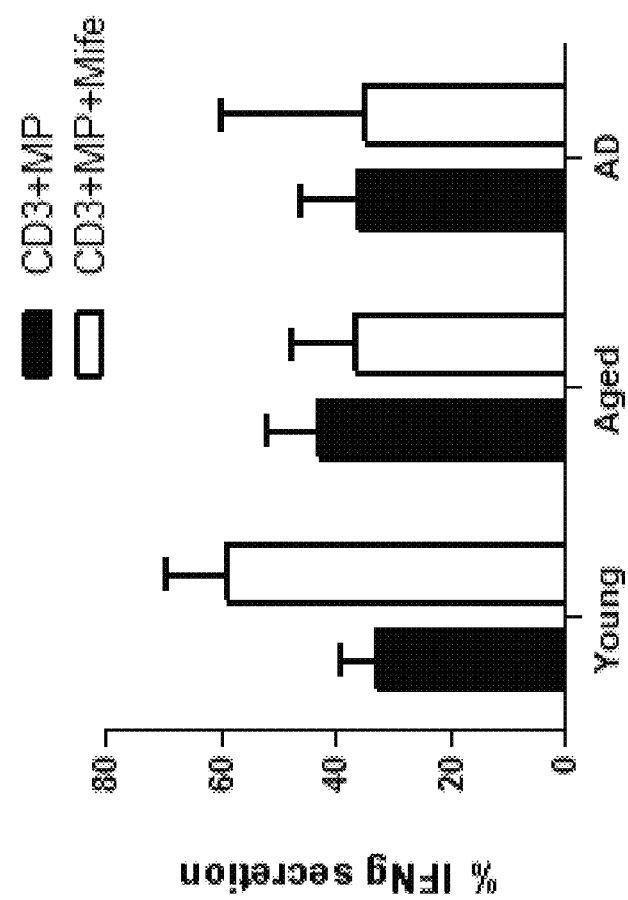
FIG. 7. Aging and Alzheimer's disease reduces the response to glucocorticoid agonist. Bar chart depicting IFNγ levels in the supernatant from young, aged and AD cells. Levels were measured using ELISA and standardized to levels without the addition of MP.

Specifically, FIG. 7 shows the capability of GR antagonist to block steroid (MP) immunosuppressive effects. PBMCs were purified from young healthy-aged and AD subjects, stimulated by plate-bound anti-CD3 mAb (0.5 micro-g/ml) for 48 hours in the presence of MP or with both MP and GR antagonist, mifepristone. The cultured supernatants were examined for IFNg production by ELISA; the results are shown as percentage of the levels measured without MP.

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove. Rather the scope of the invention is defined only by the claims which follow.

What is claimed is:

1. A kit for in-vitro evaluating resistance to a steroid in a subject in need of steroid therapy, the kit comprising at least one of:
   (a) an immune cell stimulating agent, said steroid and at least one pro-inflammatory cytokine-specific antibody, said cytokine is selected from the group consisting of: interleukin 1A (IL-1A), IL-1, IL-2, IL-6, IL-12, IL-17, tumor necrosis factor alpha (TNFα), interferon gamma (INFγ), chemokine (C-C motif) ligand 2 (CCL2)/monocyte chemotactic protein 1 (MCP-1), and chemokine (C-C motif) ligand 5 (CCL5/RANTES);
   (b) an immune cell stimulating agent, said steroid, a GR agonist, and at least one pro-inflammatory cytokine-specific antibody, said cytokine is selected from the group consisting of: IL-1A, IL-1B, IL-2, IL-6, IL-12, IL-17, IL-22, TNFα, INFγ, CCL2 (MCP-1) and CCL5 (RANTES); and said kit further comprising instructions for use configured to evaluate resistance to a steroid in a subject.

2. The kit of claim 1, wherein said steroid is selected from the group consisting of cortisol, dexamethasone and methylprednisolone (MP).

3. The kit of claim 1, wherein said immune cell is a T cells and said stimulating agent is selected from the group consisting of: anti-CD3 antibody, anti-CD28 antibody, and a combination thereof.

4. The kit of claim 1, wherein said immune cell is a monocyte and said stimulating agent is selected from the group consisting of lipopolysaccharide (LPS), other toll-like receptor (TLR) ligands, and a combination thereof.

5. The kit of claim 1, wherein said immune cell is a dendritic cell and said stimulating agent is LPS.

6. The kit of claim 1, for use in determining the level of resistance to a steroid in a subject, wherein a greater number of proinflammatory cytokine level measurements above predetermined control results indicates an increased level of resistance to said steroid.

7. The kit of claim 1, further comprising at least one reagent for protein detection for performing a method to evaluate resistance to a steroid in a subject using flow-activated cell sorting (FACS) and enzyme-linked immunosorbant assay (ELISA), tissue culture or Western blotting.

8. The kit of claim 1, wherein said glucocorticoid receptor agonist is selected from the group consisting of: dexamethasone and mifepristone.

9. The kit of claim 1, for use in evaluating resistance to a steroid due to chronic stress in the subject.

10. The kit of claim 1, for use in evaluating resistance to a steroid due to at least one of the following diseases or disorders: a mental disorder, an autoimmune disease, chronic inflammation or glucocorticoid resistance associated with a tumor or tumor micro-environment.

11. The kit of claim 10, wherein said mental disorder is selected from the group consisting of: Alzheimer's, depression, schizophrenia and aging.

12. The kit of claim 1, further comprising immune control cells having control levels selected from the group consisting of: (a) pro-inflammatory cytokine levels in supernatant from a healthy immune cell after activation and administration of a steroid; (b) cytokine levels in supernatant from a healthy immune cell after activation and administration of a steroid and GR agonist; (c) anti-inflammatory cytokine levels in supernatant from a healthy immune cell after activation and administration of a steroid.

13. The kit of claim 1, further comprising at least one anti-inflammatory cytokine-specific antibody, said cytokine is selected from the group consisting of: IL-4 and IL-10.

14. A method for evaluating resistance to a steroid and determining treatment, in a subject in need of steroid therapy, the method comprising:
  i) providing a sample from said subject comprising immune cells;
  ii) stimulating said immune cells in said sample;
  iii) contacting a portion of said stimulated immune cells with said steroid;
  iv) measuring, in supernatant from said contacted stimulated immune cells, a level of at least one pro-inflammatory cytokine selected from the group consisting of: IL-1A, IL-1B, IL-2, IL-6, IL-12, IL-17, IL-22, TNFα, INFγ, CCL2 and CCL5;
  v) wherein a significantly reduced level of the at least one pro-inflammatory cytokine in said subject, as compared to the level in supernatant from immune control cells, is indicative of steroid resistance in said subject; and
  wherein the level of steroid resistance is used as a basis of treatment of the subject in need of steroid therapy.

15. The method of claim 14, wherein said immune cell is a T-cell and said stimulating is contacting the immune cell with an agent selected from the group consisting of: anti-CD3 antibody, anti-CD28 antibody and a combination thereof.

16. The method of claim 14, wherein said immune cell is a monocyte and said stimulating is contacting the immune cell with an agent selected from the group consisting of: lipopolysaccharide (LPS), other toll-like receptor (TLR) ligands and a combination thereof.

17. The method of claim 14, wherein said immune cell is a dendritic cell and said stimulating is contacting the immune cell with LPS.

18. The method of claim 14, wherein said steroid is methylprednisolone (MP).

19. The method of claim 14, wherein said contacting said immune cell with the steroid further comprises contacting said immune cell with a glucocorticoid receptor (GR) agonist.

20. The method of claim 19, wherein said GR agonist is selected from the group consisting of: dexamethasone and mifepristone.

21. The method of claim 14, for use in determining the level of resistance to a steroid, wherein a greater difference between pro-inflammatory cytokine levels in subject immune cells and control cells indicates greater resistance to said steroid.

22. The method of claim 14, further comprising:
  i) measuring in supernatant from said contacted stimulated immune cells a level of at least one anti-inflammatory cytokine selected from the group consisting of: IL-4 and IL-10;
  ii) calculating a ratio of the pro-inflammatory cytokine level to the anti-inflammatory cytokine level; and
  (iii) diagnosing said subject with steroid resistance when the ratio is significantly increased as compared to the ratio from control immune cells.

23. The method of claim 14, further comprising:
  i) measuring the level of said cytokine, in supernatant from uncontacted stimulated immune cells;
  ii) calculating a ratio of cytokine levels from contacted immune cells and said uncontacted stimulated immune cells; and
  iii) diagnosing said subject with steroid resistance when the ratio is significantly reduced in said subject cells as compared to control immune cells.

24. A method for evaluating resistance to a steroid, in a subject in need of steroid therapy, the method comprising:
  i) providing a sample from said subject comprising immune cells;
  ii) stimulating said immune cells in said sample;
  iii) contacting a portion of said stimulated immune cells with said steroid;
  iv) measuring in supernatant from cells said contacted (a) stimulated immune and (b) said uncontacted stimulated immune cells a level of at least one pro-inflammatory cytokine selected from the group consisting of: IL-1A, IL-1B, IL-2, IL-6, IL-12, IL-17, IL-22, TNFα, INFγ, CCL2 and CCL5;
  v) comparing pro-inflammatory cytokine levels between said (a) with said steroid and (b) without said steroid to calculate a percent suppression;
  vi) diagnosing said subject with steroid resistance when percent suppression is significantly reduced in said subject immune cells as compared to healthy age-matched control immune cells; and
  wherein the level of steroid resistance is used as a basis of treatment of the subject in need of steroid therapy.

* * * * *

UNITED STATES PATENT AND TRADEMARK OFFICE
CERTIFICATE OF CORRECTION

PATENT NO. : 9,664,690 B1  
APPLICATION NO. : 14/471168  
DATED : May 30, 2017  
INVENTOR(S) : Alon Monsonego and Idan Harpaz Page 1 of 1

It is certified that error appears in the above-identified patent and that said Letters Patent is hereby corrected as shown below:

On the Title Page

Please replace the Assignee listed on the Patent, currently "THE NATIONAL INSTITUTE FOR BIOTECHNOLOGY I" with the following: "THE NATIONAL INSTITUTE FOR BIOTECHNOLOGY IN THE NEGEV LTD."

Signed and Sealed this
Third Day of October, 2017

Joseph Matal
*Performing the Functions and Duties of the*
*Under Secretary of Commerce for Intellectual Property and*
*Director of the United States Patent and Trademark Office*